United States Patent
Bolmsjöet al.

(10) Patent No.: US 6,596,017 B1
(45) Date of Patent: Jul. 22, 2003

(54) DEVICE FOR HEAT TREATMENT OF BODY TISSUE

(75) Inventors: Magnus Bolmsjö, Lund (SE); Christian Sturesson, Lund (SE); Stefan Andersson-Engels, Höör (SE)

(73) Assignee: Prostalund Operations AB, Lund (SE)

( * ) Notice: Subject to any disclaimer, the term of this patent is extended or adjusted under 35 U.S.C. 154(b) by 0 days.

(21) Appl. No.: 09/786,916

(22) PCT Filed: Sep. 9, 1999

(86) PCT No.: PCT/SE99/01569
§ 371 (c)(1),
(2), (4) Date: Aug. 27, 2001

(87) PCT Pub. No.: WO00/15131
PCT Pub. Date: Mar. 23, 2000

(30) Foreign Application Priority Data

Sep. 10, 1998 (SE) .............................................. 9803079

(51) Int. Cl.[7] .............................................. A61B 17/36
(52) U.S. Cl. .............................. 607/89; 606/15; 606/17; 607/92
(58) Field of Search ....................... 607/89, 92; 606/15, 606/16, 17

(56) References Cited

U.S. PATENT DOCUMENTS

| | | | |
|---|---|---|---|
| 5,292,320 A | | 3/1994 | Brown et al. |
| 5,366,490 A | * | 11/1994 | Edwards et al. ............ 128/898 |
| 5,437,660 A | * | 8/1995 | Johnson et al. ................ 606/15 |
| 5,496,308 A | | 3/1996 | Brown et al. |
| 5,514,669 A | * | 5/1996 | Selman ........................ 514/184 |
| 5,700,260 A | * | 12/1997 | Cho et al. ...................... 606/15 |
| 5,830,209 A | * | 11/1998 | Savage et al. ................. 606/13 |
| 5,989,283 A | * | 11/1999 | Wilkens ................... 250/493.1 |

FOREIGN PATENT DOCUMENTS

SE 0761257 A2 3/1997

OTHER PUBLICATIONS

International Search Report.
International Preliminary Examination Report.
Sturesson, C. and S. Andersson–Engels. "Tissue temperature control using a water–cooled applicator: Implications for transurethral laster–induced thermotherapy of benign prostatic hyperplasia." *American Association of Physicists in Medicine* Mar. 1997: 461–470.

* cited by examiner

*Primary Examiner*—Harold Joyce
(74) *Attorney, Agent, or Firm*—Patterson, Thuente, Skaar & Christensen, P.A.

(57) ABSTRACT

Transurethral catheter (10) for the heat treatment of body tissue surrounding the catheter, including an elongated light carrier (11). A light receiving and light distributing elongated light probe (12) is operatively connected to said light carrier (11), and the light probe (12) comprises light reflecting surfaces (13) for preventing received light from escaping from the probe (12). At least one light emitting section (14) is formed in the probe (12) for emitting light into said body tissue.

22 Claims, 2 Drawing Sheets

DEVICE FOR HEAT TREATMENT OF BODY TISSUE

TECHNICAL FIELD

Laser treatment of benign prostatic hyperplasia (BPH) is a developing, minimally invasive method. The method relies on the conversion of light absorbed by the tissue into heat, inducing irreversible tissue alterations.

PRIOR ART

Various treatment strategies exist. One of the most frequently employed technique is visual laser ablation of the prostate (VLAP), using the Nd:YAG laser and side-firing fibres for transurethral irradiation. A common procedure is to irradiate at 60 W for 60 s in four quadrants, producing rapid and selective coagulation of the hyperplastic tissue. Current side-firing fibres placed in the urethra irradiates a spot approximately 2 mm in diameter, resulting in limited lateral extension of the coagulated volume.

A drawback in this procedure is that repeated irradiation steps are required for producing coalescing lesions. The efficient heating from a concentrated beam will require an effective monitoring of the temperature development in the tissue, so as to avoid unwanted damages of other parts of the surrounding tissues. It is difficult to achieve this type of monitoring and the patient would be exposed to a higher risk than if another type of heating is used. Due to the fact that very high energies are absorbed in a small local spot, the patient needs in most cases general or spinal anesthesia.

SUMMARY OF THE INVENTION

An object of the present invention is to avoid the above specified drawback. A further object is to provide a device which at a low risk for the patient facilitates an effective treatment. These objects are achieved by a device as claimed in the independent claim.

The device according to the invention will make it possible to treat the entire length of the prostatic urethra after positioning a light probe in one single location. In a preferred embodiment this could be achieved by using a laser probe with an illumination field in the shape of a rectangular bar instead of a circular spot.

In a preferred embodiment the device is formed as a side-firing laser catheter. It will fulfill the following requirements: lateral irradiation in order to heat the lateral prostatic lobes selectively, extended length of laser emission in order to treat a large portion of the prostatic urethra in a single session, and minimized loss of laser light for good light economy. Other right sources may also be used.

Further objects and advantages of the invention are shown in the description below and in the accompanying drawings and dependent claims.

BRIEF DESCRIPTION OF THE DRAWINGS

The invention will be understood from the following description of embodiments thereof given by way of example only with reference to the accompanying drawings in which.

DETAILED DESCRIPTION

Figure 1:
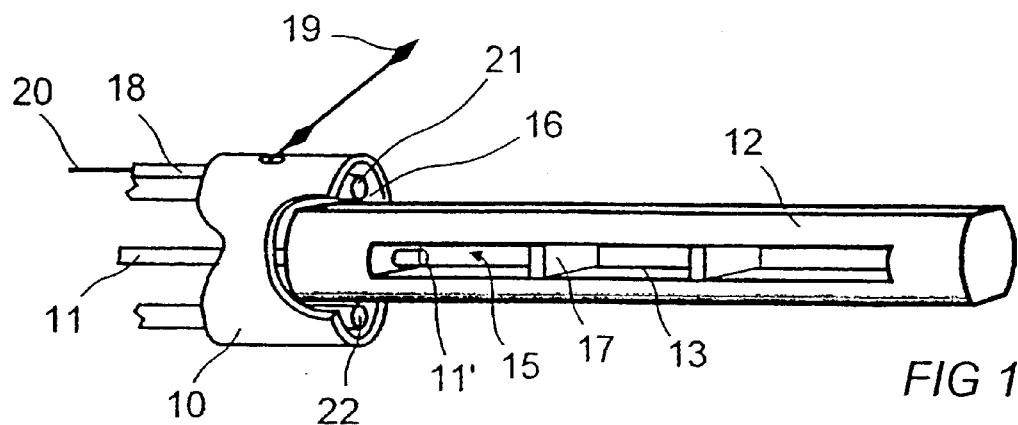
FIG. 1 is a schematic perspective view of one embodiment of a device according to the invention.

In the embodiment shown In FIG. 1 a transurethral catheter 10 is partly cut to show an elongated light carrier 11 and laser probe 12. The light carrier 11 preferably is an optical fibre. The laser probe is fabricated from a 6 mm diameter and 35 mm long cylinder of a highly diffuse reflective, plastic material, (SPECTRALON, LABSPHERE, NORTH SUTTON, N.H.). A 1 mm wide and 28 mm long slit 15 has been cut in the probe. A small hole is drilled in one end-face of the cylinder to permit the insertion of a 600 µm core diameter optical fibre. The fibre extends a few mm into the slit with an end part 11'. The cylinder is flattened parallel to the slit 15 to allow circulation of cooling water around the probe in two semicircular spaces, 16 formed between the probe 12 and the catheter 10. The width of the catheter wall in this embodiment is approximately 1 mm. Light entering the slit from the fibre will scatter on surfaces surrounding the slit and finally exit through the slit opening.

Preferably the laser probe 12 is flexible, so as to be readily inserted within the prostate tissue through the urethra. In the location of treatment the probe may be bent and preferably the probe operates with the same effect in such a position. In an embodiment where the probe is formed with a slit 15 it may be necessary or at least appropriate to provide distance elements 17 which will maintain the slit dimensions even when the probe is bent. Preferably, the distance elements 17 are made of translucent material, so as not to deteriorate the light emitting properties of the probe. In the embodiment shown the distance elements extend transverse to the longitudinal direction of the probe, but it may be appropriate to provide a distance element extending in the longitudinal direction of the probe. It is also possible to provide a distance element 17 completely filling up the slit 15.

Figure 6:
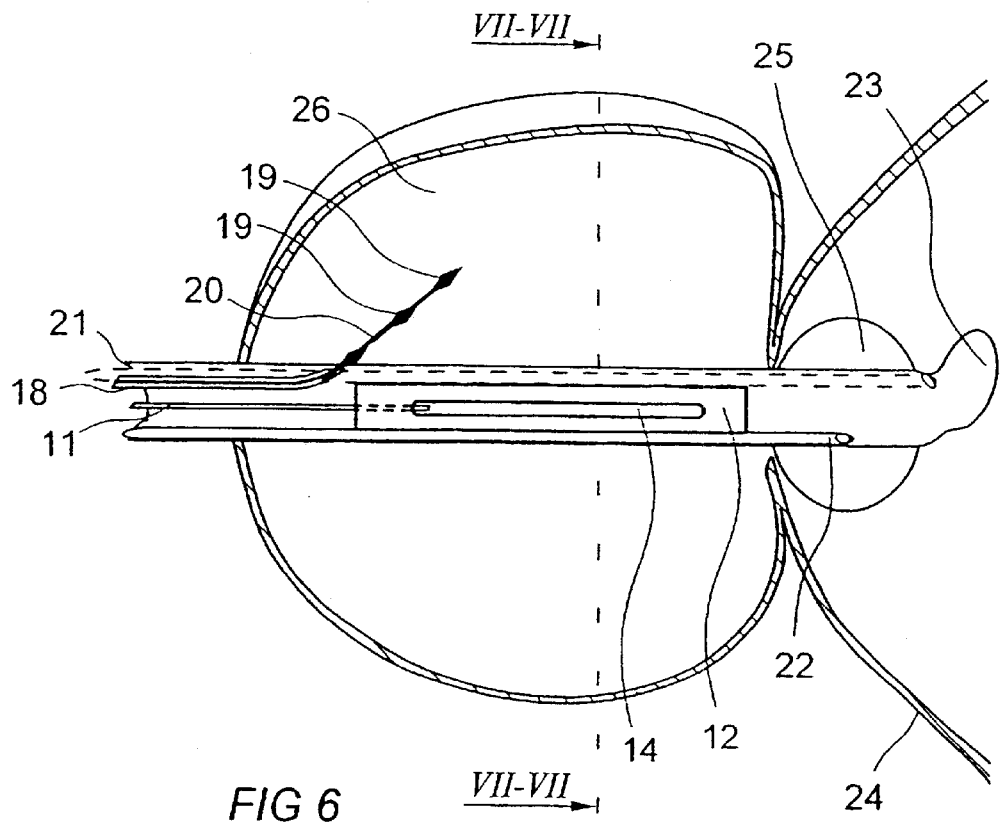
FIG. 6 is a schematic side view partly in section of the device in FIG. 5 at a location of treatment in the human body.

In the catheter shown there is also provided a first tubular carrier 18 for a set of temperature transducers 19 (see also FIG. 6). The temperature transducers 19 are supported on a wire 20 which can be extended from an opening in the catheter 10. A second tubular means 21 can be used for draining the bladder (see FIG. 6) and a third tubular means 22 can be used to inflate a balloon (see FIG. 6) which is used to maintain the catheter in a desired position. The probe will transmit up to 95% of the power emitted by the plane-cut optical fibre. By painting the outer aspect of the probe with opaque, reflective paint, the emission through the slit will be up to 80%.

Figure 2:
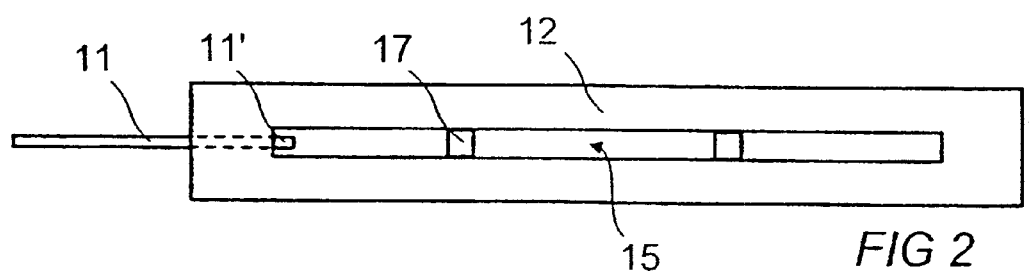
FIG. 2 is a side elevation view of the device in FIG. 1.
Figure 3:
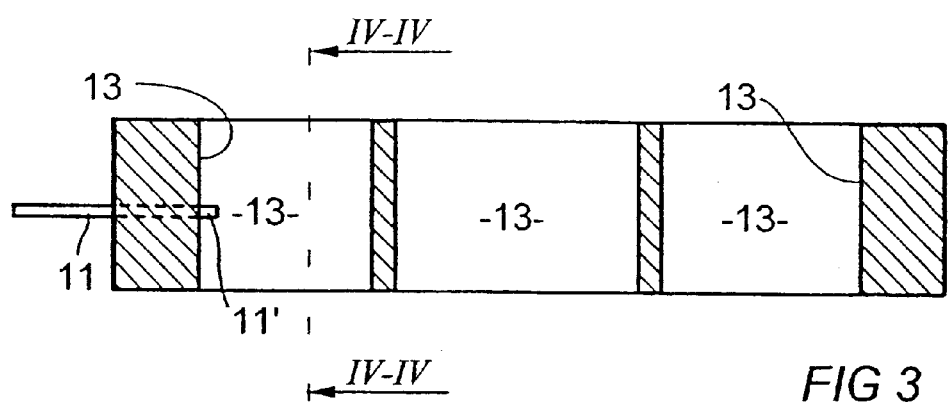
FIG. 3 is a longitudinal sectional view of the device in FIG. 1.

In FIG. 2 and FIG. 3 the probe 12 and the distance elements according to one embodiments are shown in more detail. It can also be seen that the light carrier 11 extends into the slit 15.

Figure 4:
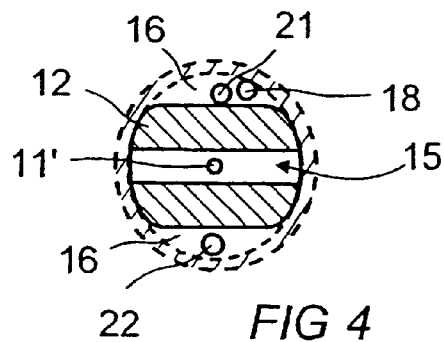
FIG. 4 is a cross sectional view of the device in FIG. 1.

The cross sectional view in FIG. 4 shows the laser probe 12 centrally located within the catheter 10. The second and third tubular means 21 and 22 are located in the semicircular spaces 16 on either side of the laser probe 12. The water that is circulated through the semicircular spaces 16 is used to cool the probe 12, so as to avoid heating of the anterior and posterior parts of the prostate. Water at a temperature of 5–20° C. can be flushed through the catheter. An appropriate rate is approximately 100–1000 ml/min Using a 10–60 W Nd YAG laser the treatment will be performed for a few minutes up to an hour. It is also possible to use other types of laser, e.g. diode laser, or a non-coherent light source.

Figure 5:
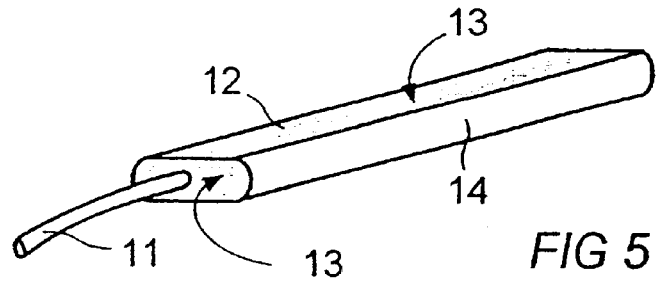
FIG. 5 is a side elevation view of an alternative embodiment of a device according to the invention.

A second embodiment of a laser probe according to the invention is shown in FIG. 5. In this embodiment the complete probe 12 is made from a translucent flexible material, such as clear silicon, polycarbonate (with an appropriate plasticizer) and polyethylene. Besides two light emitting sections 14 on opposite sides of the probe 12 the complete exterior of the probe 12 is covered by a fight reflecting layer. Preferably the reflecting layer is formed by a highly reflective material, such as aluminum. The light carrier 11 extends into the probe and light will propagate within the probe to be repeatedly reflected by the reflecting layer. A major part of the light will firmly be emitted though the light emitting section 14. In a simple embodiment the two light emitting sections 14 on opposite sides of the probe 12 extends over the complete side sections of the probe 12. The dimensions of the side sections will correspond to the dimensions of the slits 15 in the embodiment according to FIGS. 1–4.

In FIG. 6 the catheter 10 has been inserted through the urethra to a position where a tip 23 of the catheter is located in the bladder 24. A balloon 25, also located inside the bladder, has been inflated. In this position and condition the balloon will maintain the catheter in position and ensure that the catheter cannot be withdrawn unintentionally. The balloon 25 is inflated through one of the tubular means. Another tubular means opens into the bladder and will permit a drain of the bladder during and optionally after the treatment.

In position the laser probe 12 is located centrally in the prostate 26 or as shown in FIG. 6 closer to the bladder neck. The wire 20 carrying the temperature transducers has been extended through the catheter at an appropriate angle in relation to the longitudinal direction of the catheter.

Figure 7:
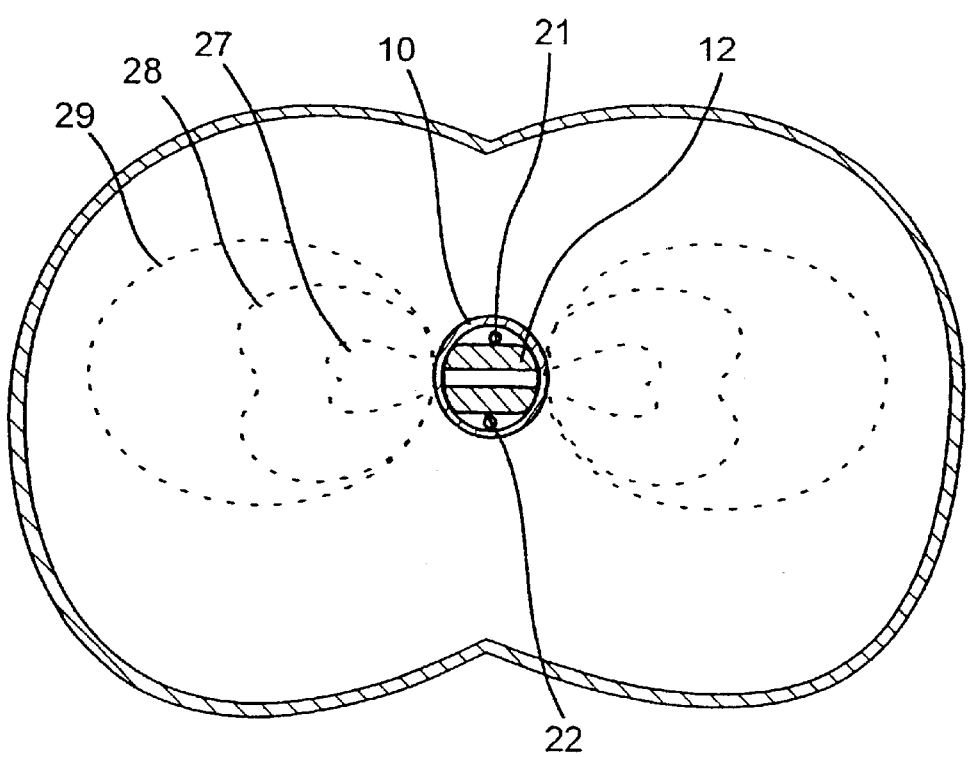
FIG. 7 is a cross sectional view of the device in FIG. 6.

FIG. 7 shows schematically the temperature distribution in the prostate tissue. Light is emitted in four lobes. No light is emitted in the anterior or the posterior direction. The irradiated area will have the same rectangular shape as the slit by keeping the distance between the probe and the tissue surface short. Near the catheter wall, high temperatures are found in the laser-irradiated areas. Further out, the temperature distribution is more elliptical due to heat conduction.

In transverse cross-section, the temperature distribution close to the catheter wall is butterfly-shaped as shown at 27. This is valid also at some distance from the catheter as shown at 26. Further out, the distribution become elliptical, as shown at 29.

The side-firing laser catheter according to the invention has been developed with the intention to permit selective coagulation by selective laser irradiation of the hyperplastic prostate over the entire length of the prostatic urethra after placement of the catheter in one single position. The present probe relies on diffuse reflectance, while conventional side-firing fibres are equipped with gold-plated mirrors or utilise the principle of internal reflection.

The laser probe is inserted into a catheter with integrated water cooling, which is intended to be positioned within the prostatic urethra under, transrectal ultrasound guidance. Light is emitted in many directions through the slit but local tissue irradiation is achieved by ensuring that there is only a short distance between the slit opening and the urethral wall.

The area of the irradiated tissue surface is close to the area of the slit. Water circulation is employed to cool the laser prove and to permit deep thermal coagulation. The cooling will result in that the maximum temperature is forced a few millimeters into the tissue, which makes it possible to coagulate larger volumes without inducing carbonisation.

Without cooling, the catheter surface would reach the highest temperatures. The temperature of the cooling fluid should be chosen so as to force the temperature rise deep into the tissue without causing carbonisation of the urethra. The cooling water temperature typically will be 5–20° C.

Longitudinally, in the plane of fight emission, a tissue area extending more than 30 millimeters can be treated, which in vivo would enable rapid coagulation. The longitudinal extension of the temperature distribution depends on the length of the laser probe. Longer probes can be used for treatment of longer prostates.

The transverse cross-sectional temperature distribution will be elliptical a few millimeters from the catheter wall. Due to heat conduction, the temperature distribution becomes more and more circular when irradiating for longer times (result not shown). The shorter the duration of the treatment, the greater the difference in temperature between the laser irradiated areas and the areas shielded from direct laser irradiation. However, too short a treatment limits the tissue volume raised to therapeutic temperatures.

The laser power should thus be chosen as high as possible without inducing carbonisation, which may lead to catheter destruction. With this setting, coagulation of the urethra will occur, as is the case in VLAP.

What is claimed is:

1. A transurethral catheter for the heat treatment of body tissue surrounding the catheter, comprising an elongated light carrier, a light receiving and light distributing elongated light probe operably connected to said light carrier, the light probe comprising light reflecting surfaces for preventing received light from escaping from the probe, and at least one elongated light emitting section formed in the probe, the light emitting section presenting a light emitting section longitudinal axis and structure for directing the emission of light directionally, radially outwardly from the light emitting section along said light emitting section longitudinal axis for simultaneously emitting light into said body tissue along a desired length of body tissue.

2. The transurethral catheter according to claim 1, wherein the probe is made of a light diffusing material, a light reflective material or a light diffusing and reflective material and the light emitting section is a slit in the probe for the escape of light.

3. The transurethral catheter according to claim 2, wherein a plurality of slits are provided in the probe for distributing light in different directions.

4. The transurethral catheter according to claim 2, wherein the slit extends over substantially the complete length of the probe.

5. The transurethral catheter according to claim 1, wherein the probe is made of a translucent material and the light reflecting surfaces are formed by light reflecting layers on the surfaces of the probe, and wherein the light emitting sections are sections of bare translucent material.

6. The transurethral catheter according to claim 5, wherein a plurality of bare sections are provided on the probe for distributing light in different directions.

7. The transurethral catheter according to claim 1, further comprising means for cooling at least the light probe.

8. The transurethral catheter according to claim 1, further comprising at least one temperature transducer arranged to be extended from the catheter into the tissue to be treated.

9. The transurethral catheter according to claim 8, wherein the temperature transducer is carried by a wire extendible through an opening in the catheter.

10. The transurethral catheter according to claim 1, further comprising a balloon for fixing the catheter in a desired location.

11. A method of heat treating a length body tissue surrounding a catheter the method comprising the steps of:

inserting a catheter into the tissue, the catheter comprising an elongate light carrier, an elongate light receiving and distributing probe operably connected to the light carrier, the probe comprising light reflecting surfaces for preventing received light from escaping from the probe and one or more elongate light emitting sections formed into the probe for emitting light into the body tissue, the light emitting section presenting a light emitting section longitudinal axis and structure for directing the emission of light directionally, radially outwardly from the light emitting section along said light emitting section longitudinal axis for simultaneously emitting light into said body tissue along a desired length of body tissue;

transmitting light for heat treating the tissue via the light carrier to the light probe thereby heating the tissue;

maintaining the light transmission for a therapeutically effective interval of time; and removing the catheter from the tissue.

12. The method as claimed in claim 11 further comprising the step of circulating coolant proximate the catheter.

13. The method as claimed in claim 11 further comprising the step of inserting a temperature transducer into the tissue, the temperature transducer being extended from the catheter upon insertion of the catheter into the tissue.

14. The method as claimed in claim 11 further comprising the step of providing a wire on the catheter and extending a temperature transducer on the wire.

15. The method as claimed in claim 11 further comprising the steps of providing a balloon operably connected to the catheter and inflating the balloon to maintain the catheter in position.

16. The method as claimed in claim 11 in which the transmitted light is laser light.

17. A transurethral catheter for heat treatment of a length prostate tissue surrounding the catheter, comprising;

an elongated light carrier;

an elongate optically translucent light probe operably connected to said light carrier;

the light probe comprising light reflecting surfaces for preventing received light from escaping from the probe; and at least one elongate directional light emitting section for emitting light into said body tissue, the light emitting section presenting a light emitting section longitudinal axis and structure for directing the emission of light directionally, radially outwardly from the light emitting section along said light emitting section longitudinal axis for simultaneously emitting light into said body tissue along a desired length of body tissue.

18. The transurethral catheter as claimed in claim 17, further comprising a balloon for maintaining the catheter in position.

19. The transurethral catheter as claimed in claim 17, further comprising a coolant circulating member for circulating coolant proximal to the light probe.

20. The transurethral catheter as claimed in claim 17, further comprising a temperature sensor retractably insertable into the tissue for sensing the temperature thereof.

21. The transurethral catheter as claimed in claim 17, in which the light emitting section is adjacent to a cavity within the light probe, the cavity having one or more openings locatable proximate the tissue.

22. The transurethral catheter as claimed in claim 17, in which the light emitting section is a portion of the translucent probe free of the light reflecting surface.

* * * * *